United States Patent [19]

Okuno

[11] 4,009,281
[45] Feb. 22, 1977

[54] FUMIGANT COMPOSITION CONTAINING D-ALLETHRONYL D-TRANS-CHRYSANTHEMATE

[75] Inventor: Yoshitoshi Okuno, Toyonaka, Japan

[73] Assignee: Sumitomo Chemical Company, Limited, Osaka, Japan

[22] Filed: Sept. 29, 1975

[21] Appl. No.: 617,711

Related U.S. Application Data

[63] Continuation of Ser. No. 459,934, April 11, 1974, abandoned.

[30] Foreign Application Priority Data

Apr. 21, 1973 Japan .............................. 48-45513

[52] U.S. Cl. .............................................. 424/306
[51] Int. Cl.$^2$ ........................................ A01N 9/24
[58] Field of Search .................................. 424/306

[56] References Cited

UNITED STATES PATENTS

| | | | |
|---|---|---|---|
| 3,009,946 | 11/1961 | Takei et al. | 424/306 |
| 3,186,903 | 6/1965 | Soltes | 424/306 |
| 3,636,059 | 1/1972 | Matsui et al. | 424/306 |
| 3,641,245 | 2/1972 | Epstein | 424/306 |
| 3,723,615 | 3/1973 | Okuno | 424/306 |
| 3,766,218 | 10/1973 | Ueda et al. | 427/306 |

FOREIGN PATENTS OR APPLICATIONS 1,092,912  11/1960  Germany

OTHER PUBLICATIONS

J. Econ. Entmol 46 p. 999 (1953) Gersdorfl et al.

Primary Examiner—Albert T. Meyers
Assistant Examiner—D. W. Robinson
Attorney, Agent, or Firm—Stevens, Davis, Miller & Mosher

[57] ABSTRACT

A novel insecticidal composition in the form of fumigant which comprises, as an active ingredient, d-2-allyl-3-methyl-cyclopent-2-ene-1-one-4-yl d-trans-chrysanthemate consisting of d-allethrolone and d-trans-chrysanthemic acid, and an inert carrier, which has a rapid knock down effect and an effect to delay the recovery of injurious insects knocked down, and which is useful for sanitary, agricultural and horticultural purposes.

2 Claims, 4 Drawing Figures

FIG. I
RELATION BETWEEN LAPSE OF TIME AND $KT_{50}$

RELATION BETWEEN LAPSE OF TIME AND $KT_{50}$

RELATION BETWEEN CONCENTRATION AND $KT_{50}$

FUMIGANT COMPOSITION CONTAINING D-ALLETHRONYL D-TRANS-CHRYSANTHEMATE

This is a continuation of application Ser. No. 459,934 filed Apr. 11, 1974, now abandoned.

This invention relates to a novel insecticidal composition in the form of fumigant which contains as an active ingredient d-2-allyl-3-methyl-cyclopent-2-ene-1-one-4-yl d-trans-chrysanthemate.

The object of the present invention is to provide a novel insecticidal composition in the form of fumigant which has a rapid knock-down effect and an effect to delay the recovery of injurious insects knocked down, and which is useful for sanitary, agricultural and horticultural purposes.

In the present invention, the effect to delay the recovery of injurious insects knocked down in hereinafter referred to as the persistent effect, and the fumigant means such composition as produce the vapor of the active ingredient by means of heating.

As insecticides for environment sanitation, oil sprays, aerosols, emulsifiable concentrates and dusts of pyrethrin and allethrin have widely been used heretofore because of their low toxicity to mammals and a rapid knock-down effect.

In order to obtain an insecticide having more effective insecticidal activity with low toxicity to mammals, compared with that of the conventional insecticides, the present inventor has extensively studied and attained to the knowledge that an ester consisting of d-allethrolone and d-trans-chrysanthemic acid (hereinafter referred to as the present ester) can display a specifically high insecticidal activity when used as the fumigant, which is entirely different in application condition from oil sprays, aerosols, etc. Such knowledge cannot easily be inferred theoretically as well as from the knowledge on the insecticidal activity of said ester in the form of an oil spray or the like.

The inventor has found that when used the present ester in the form of a mosquito coil, an electric mosquito killer mat or an insect fogger which are necessarily subjected to heating, the present ester has several times the knock-down effect of an optically active allthronyl chrysanthemate consisting of dl-allethrolone and d-trans-chrysanthemic acid, and found that even when used in a practical state such as a dilute fumigant, the present ester can maintain its insecticidal activity to mosquito or cockroaches for such a long period of time as can not be anticipated from a conventional electric mosquito killer mat of this kind.

Thus, the present invention is to provide an insecticidal composition in the form of the fumigant containing as an active ingredient an effective amount of d-2-allyl-3-methyl-cyclopent-2-ene-1-one-4-yl d-trans-chrysanthemate obtained by the reaction of d-allethrolone and d-trans-chrysanthemic acid, and an inert carrier. The effective amount is within a range of 0.05 to 90% by weight based on the total amount of composition and preferably 0.05 to 50% weight. More particularly, it is preferable that the effective amount of the electric mosquito killer mat is 0.5 to 20% by weight, the effective amount of oil spray or emulsion for the insect fogger is 0.05 to 50% by weight and the effective amount of the mosquito coil is 0.05 to 5% by weight.

Various examinations have been made with respect to the relation between the allethrin isomers and the insecticidal activity, and it is well known that commercially available allethrins are mixtures of 8 isomers and, among these, an ester comprising d-allethrolone and d-trans-chrysanthemic acid displays the highest insecticidal activity which has 3.86 times the insecticidal activity of the allethrin product, when used in the form of an oil spray [W. A. Gersdorff and Narman Mitilin: J. Econ. Entmol., 46, page 999 (1953)].

It is also well known that in order to obtain an allethrin which is higher in insecticidal activity than that of the allethrin product available at present, there may be prepared an ester consisting of dl-allethrolone and d-trans-chrysanthemic acid. For example, Ryo Yamamoto: "Noyakugaku (Agricultural Chemicals)" (published by Nanko-do on Mar. 15, 1963) describes on page 73 that the insecticidal activity on houseflies of the d-trans-chrysanthemic acid ester with dl-allethrolone is about 2 times the activity of the ester consisting of dl-allethrolone and dl-cis,trans-chrysanthemic acid, and recommends to use the ester of d-trans-chrysanthemic acid in order to enhance the insecticidal activity of the allethrin product.

The present inventor also tested the insecticidal activity of the individual chemicals on housefly adults and those of oil sprays thereof on housefly adults and Northern house mosquito adults to obtain the results that the insecticidal activity of the d-trans-chrysanthemic acid ester with dl-allethrolone is about 2.4 times the activity of allethrin, which well coincided with the results stated by Ryo Yamamoto. And the insecticidal activity of d-trans-chrysanthemic acid ester with d-allethrolone is about 4 times the activity of commercial allethrin, which also well coincided with the results stated by W. A. Gersdorff et al.

Until today, however, the ester using d-trans-chrysanthemic acid and d-allethrolone has not been put into practical use. This is ascribable to the fact that when used in the form of an oil spray, the ester of d-trans-chrysanthemic acid and d-allethrolone, which has not more than about 4 times the insecticidal activity of the ordinary allethrin product, is too low in the insecticidal activity, in view of the production cost thereof, to be practically used in place of the allethrin product which is commercially available at present.

The surprising is a finding that when used in the form of fumigant such as a mosquito coil, an electric mosquito killer mat or an insect fogger, the present ester gives an insecticide having more rapid knock-down and more persistent effects which are most important for the control of injurious insects, and which cannot be anticipated from the field of conventional studies on allethrin isomers. The present inventor has completed the present invention on the basis of such confirmation that when formulated into the fumigant, the present ester gives an insecticidal composition having such rapid knock-down effect as about 4 times the effect of the practically usable allethronyl d-trans-chrysanthemate and having the prominent persistent effect for a long period of time, and that the present insecticidal composition is more advantageous in cost and more excellent in effects than that of the d-trans-chrysanthemate of dl-allethrolone.

The present ester, d-2-allyl-3-methyl-cyclopent-2-ene-1-one-4-yl d-trans-chrysanthemate $[\alpha]_D^{24}$ −31.2 (n-Hex) having the formula,

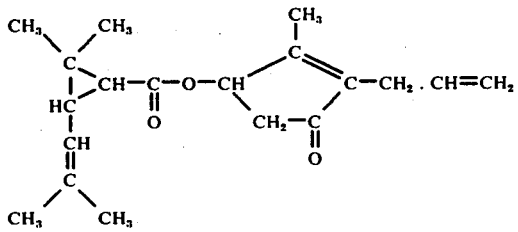

can be obtained easily in a high yield by reacting, in the presence of such a dehydrochlorinating agent as pyridine, d-allethrolone represented by the structural formula (I),

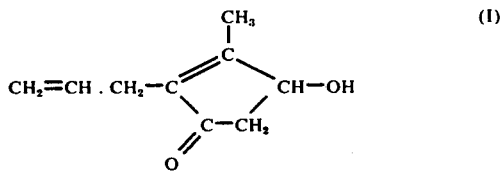

with a d-trans-chrysanthemic acid halide represented by the general formula (II),

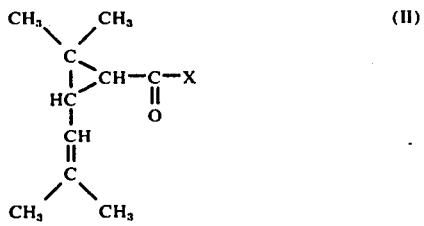

wherein X is a halogen atom.

The present insecticidal compositions which contain the present ester as an active ingredient are not only usable as domestic insecticides for the control of such sanitary injurious insects as houseflies, mosquitoes, etc., and other injurious insects in the mat houses, but also widely applicable to greenhouses, vinylhouses and storehouses to control stored cereal-injurious insects and agricultural and horticultural injurious insects.

In the accompanying drawings.

Figure 1:
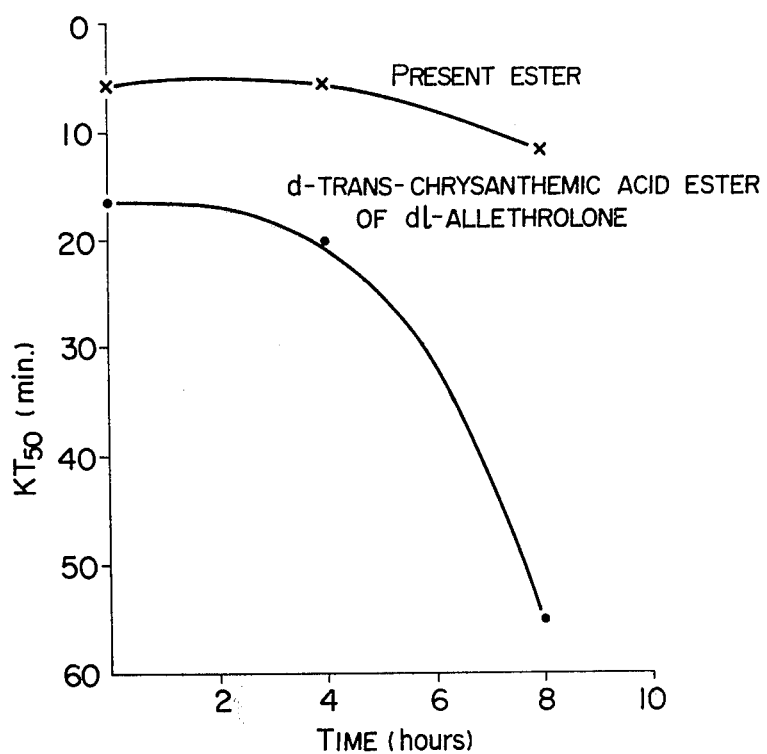
FIG. 1 shows the relation between a lapse of time and $KT_{50}$ in the knock-down effect of the electric mosquito killer mat on Northern house mosquito adults.

In order to clarify the fact that the present invention cannot be anticipated from the conventional examinations on insecticidal activity of allethrin isomers, experimental examples and results thereof are set forth below.

EXPERIMENTAL EXAMPLE 1

Allethrin (an ester consisting of dl-allethrolone and dl-cis,trans-chrysanthemic acid), d-trans-chrysanthemic acid ester of dl-allethrolone and the present ester were individually adjusted by means of acetone to a test concentration, and tested in insecticidal effects according to a process in which the acetone solution was applied at the dorsum of prothorax of the adult fly using a special microsyringe. As the result, the 50% lethal doses ($LD_{50}$) of the individual test solutions were as shown in Table 1.

Table 1

| Test compound | $LD_{50}$ (λ/fly) | Relative effect (at $LD_{50}$) |
| --- | --- | --- |
| Allethrin | 0.85 | 1.0 |
| d-trans-chrysanthemic acid ester of dl-allethrolone | 0.355 | 2.4 |
| Present ester | 0.215 | 4.0 |

EXPERIMENTAL EXAMPLE 2 d-trans-Chrysanthemic acid ester of dl-allethrolone (same as in Experimental Example 1) and the present ester were individually dissolved in deodorized kerosene to prepare 0.1% by weight oil spray, and 0.7 ml. of each of the resulting solutions was sprayed by means of an atomizer into a (70 cm)³ glass chamber. Into the glass chamber had previously been liberated 20 adults per group of Northern house mosquitoes which has elapsed 2 to 3 days after emergence or of houseflies which had elapsed 3 to 5 days after emergence. After the spraying, the knock-down state of the insects was observed at intervals of definite period of time. As the result, the 50% knock-down times ($KT_{50}$) were as shown in Tables 2 and 3.

Table 2

(Effects on Northern house mosquito adults)

| Test Compound | Concentration (% by weight) | $KT_{50}$ (sec.) | Relative effect (at $KT_{50}$) |
| --- | --- | --- | --- |
| d-trans-chrysanthemic acid ester of dl-allethrolone | 0.1 | 178 | 1.0 |
| Present ester | 0.1 | 100 | 1.8 |

Table 3

(Effects on housefly adults)

| Test Compound | Concentration (% by weight) | $KT_{50}$ (sec.) | Relative effect (at $KT_{50}$) |
| --- | --- | --- | --- |
| d-trans-chrysanthemic acid ester of dl-allethrolone | 0.1 | 248 | 1.0 |
| Present ester | 0.1 | 115 | 2.2 |

The results shown in the above Experimental Examples 1 and 2 well coincide with the results of examination of conventional allethrin isomers, and the insecticidal effect ratio of the present ester, either as it is or in the form of oil spray, to commercial allethrin or to d-trans-chrysanthemic acid ester of dl-allethrolone is about 4 times or about 2 times, respectively.

In the next place, the effects of the present ester as heating fumigants are shown below with reference to Test Examples 1 and 2.

TEST EXAMPLE 1

A piece of filter paper (0.6 g) having 2 × 3.5 cm in area and 0.2 cm in thickness was impregnated with acetone solutions of 50 mg each of d-trans-chrysanthemic acid ester of dl-allethrolone and the present ester respectively to prepare each electric mosquito killer mat (heating fumigant). There was provided a (6ft)³ Peet Grady chamber according to the U.S. CSMA standard, which is equipped with a metal plate in an inner part and a plate in a lower part, which can be heated continuously to 130° C by means of an electric heater. Each heating fumigant was placed respectively on said plate, which was thereafter heated by means of said electric heater. After the current application, 50 Northern house mosquito adults were liberated in the chamber and the flies knocked down were counted according to the lapse of 2 hours to calculate $KT_{50}$ value (50% knock-down time). Further, the mosquitoes knocked down within a period of 2 hours were collected and allowed to stand for 1 day at room temperature in an observation cage, in which a bait had been placed, and the number of killed insects was counted to calculate the ratio of killed insects. Moreover, the electric mosquito killer mat was removed out present ester is 4 times that of d-trans-chrysanthemic acid ester of dl-allethrolone, and in comparison with the Experimental examples 1 and 2, the fact described above is much surprising. Therefore, the insecticidal activity of the present ester is superior to such the known insecticide as d-trans-chrysanthemic acid ester of dl-allethrolone.

TEST EXAMPLE 2

At the bottom of a glass cylinder having 20 cm in diameter and 40 cm in height was placed the electric mosquito killer mat as used in Test Example 1. On the glass cylinder, a glass cylinder having 20 cm in diameter and 20 cm in height covered by 15 mesh-nylon net at both top site and bottom site was put, and into the upper glass cylinder were liberated 20 German cockroaches. After the current application to the lower electric mosquito killer mat, the German cockroaches knocked down were counted according to the lapse of time to calculate $KT_{50}$ value (50% knock-down time). The results are as shown in the following Table 5.

Table 5

| Test Compound | (Effects on German cockroaches by electric mosquito killer mat) | | | | | | |
|---|---|---|---|---|---|---|---|
| | Knock-down (%) According to the lapse of time | | | | | $KT_{50}$ (min.sec) | Relative Effect |
| | 5' | 10' | 20' | 40' | 60' | | |
| d-trans-chrysanthemic acid ester of dl-allethrolone | 0 | 0 | 10 | 35 | 55 | 55'00" | 1.0 |
| Present ester | 10 | 35 | 65 | 95 | 100 | 13'36" | 4.0 | of the chamber, placed into draft chamber and allowed to stand for 2 hours under current application. After Peet Grady chamber was ventilated and washed, knock-down effect on Northern house mosquito and the ratio of killed insects were calculated in the period of from 4 hours to 6 hours and from 8 hours to 10 hours after starting time to examine persistent insecticidal activity of the electric mosquito killer mat over 10 hours. The results are as shown in the following Table 4.

TEXT EXAMPLE 3

Each 5 parts by weight of d-trans-chrysanthemic acid ester of dl-allethrolone and the present ester, and each 25 parts by weight of piperonyl butoxide was individually dissolved in deodorized kerosene to make the whole 100 parts in order to obtain each oil spray.

Then, each solution obtained by diluting the oil spray prepared above 100 times with deodorized kerosene and each 3 g of the diluted oil spray was fogged by Table 4

| | (Effects or Northern house mosquito adults by electric mosquito killer mat) | | | | | | | | |
|---|---|---|---|---|---|---|---|---|---|
| | 0 – 2 hours | | | 4 – 6 hours | | | 3 – 10 hours | | |
| Test Compound | $KT_{50}$ (min.sec) | K.D. (%) after 2 hours | Kill % | $KT_{50}$ (min.sec) | K.D. (%) after 2 hours | Kill % | $KT_{50}$ (min.sec) | K.D.(%) after 2 hours | Kill % |
| d-trans-chrysanthemic acid ester of dl-allethrolone | 16'30" | 78 | 78 | 20'00" | 80 | 39 | 55'00" | 61 | 14 |
| Present ester | 5'40" | 100 | 100 | 5'30" | 100 | 100 | 11'30" | 95 | 42 |
| Relative effect ($KT_{50}$) | | 2.9 | | | 3.6 | | | 4.9 | |

As is clear from the above Test Example 1, the present ester is shorter in 50% knock-down time ($KT_{50}$) and is more rapid in knock-down effect than d-trans-chrysanthemic acid ester of dl-allethrolone. Further, relative effect on mosquito of the present ester increases about 3 times to about 5 times during a period after ignition, $KT_{50}$ value of the present ester does not decrease so much according to the time from ignition as is clear from the FIG. 1, and moreover, the present ester can maintain a high knock-down effect over a long period of time. Relative effect on cockroach of the means of an Insect Fogger produced by Burgess Vibrocrafters INC., into Peet Grady chamber according to the U.S. CSMA standard wherein about 100 houseflies were liberated in advance and the flies knocked down were counted with the lapse of time for 20 minutes to calculate $KT_{50}$ value (50% knock-down time). After 20 minutes, the air in the chamber was exchanged, the house flies knocked down were collected and allowed to stand for 1 day in an observation cage, in which a bait had been placed, and the number of killed flies was counted to calculate the ratio of killed flies. On the other hand, each 3 g of the 100 times dilution oil sprays was first fogged into the Peet Grady chamber and 20 minutes thereafter, 100 houseflies were liberated. The flies knocked down were counted with the lapse of time for 20 minutes and the number of killed flies was counted to calculate the ratio of killed flies by the same way described above.

According to results obtained, each $KT_{50}$ value and Mortality after 1 day are shown in the following Table 6.

Figure 2:
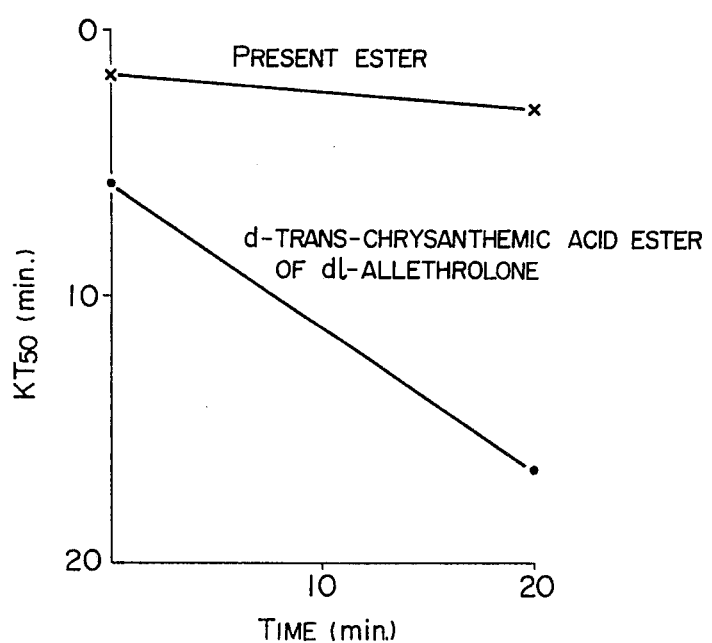
FIG. 2 shows the relation between time and $KT_{50}$ in the knock-down effects of the oil sprays on housefly adults.
Figure 3:
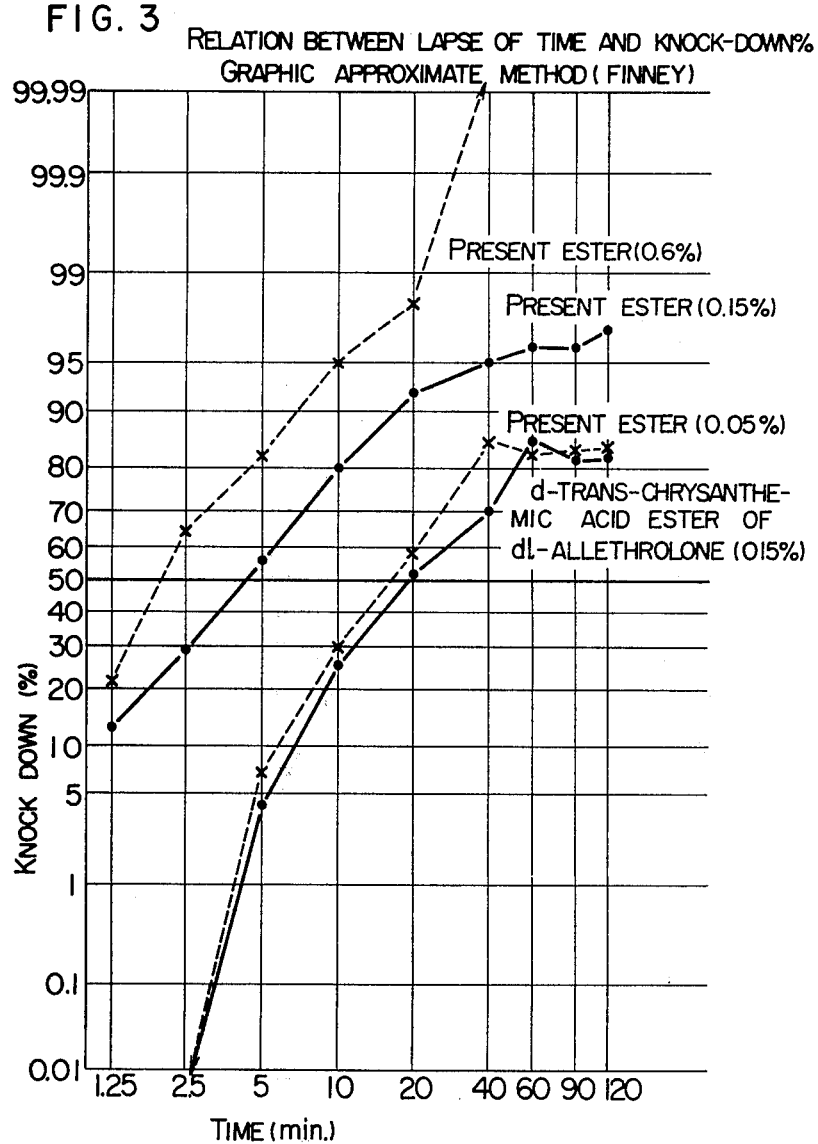
FIG. 3 shows the relation between time and $KT_{50}$ in the knock-down effects of the mosquito coils on Northern house mosquito adults.

As is clear from the above Tables 6 and 7, the present ester has 3.6 – 5.9 times higher activity than d-trans-chrysanthemic acid ester of dl-allethrolone, and as is clear from the FIG. 2, the present ester has less reduced ratio of activity during a period and moreover can maintain its activity for longer time.

TEST EXAMPLE 5

Mosquito coils each containing 0.15% by weight of d-trans-chrysanthemic acid ester of dl-allethrolone and Table 6

| Test Compounds | After liberation (min) | (Fogging effect on housefly adults) | | | | | $KT_{50}$ (min) | Relative effect | Mortality (%) |
| --- | --- | --- | --- | --- | --- | --- | --- | --- | --- |
| | | Knock-down (%) | | | | | | | |
| | | 1.25' | 2.5' | 5' | 10' | 20' | | | |
| d-trans-chrysanthemic acid ester of dl-allethrolone | 0 | 0 | 12 | 40 | 31 | 96 | 5.8 | 1.0 | 72 |
| Present ester | 0 | 43 | 65 | 88 | 100 | 100 | 1.6 | 3.6 | 100 |
| d-trans-chrysanthemic acid ester of dl-allethrolone | 20' | 0 | 0 | 10 | 32 | 57 | 16.5 | 1.0 | 4 |
| Present ester | 20' | 14 | 48 | 73 | 95 | 100 | 2.8 | 5.9 | 90 |

TEST EXAMPLE 4

Each 30 parts by weight of d-trans-chrysanthemic acid ester of dl-alletrolone, the present ester, and piperonyl butoxide was individually dissolved in deodorized kerosene to make the whole 100 parts to obtain each oil spray. Then, each solution was obtained by diluting the oil spray prepared above 50 times with deodorized kerosene, and each 3 g of the diluted oil spray was fogged by means of an Insect Fogger produced by Burgess Vibrocrafters INC., into Peet Grady chamber according to the U.S. CSMA standard wherein two dishes having 14 cm in diameter and 7 cm in height and including each 10 German cockroaches in them were placed at the bottom of the chamber. The cockroaches knocked down were counted with the lapse of time for 20 minutes and 20 minutes thereafter the air in the chamber was exchanged and the whole cockroaches knocked down were removed into the feeding cage in which a bait has been placed, and allowed to stand for 3 days and the number of killed cockroaches was counted to calculate the ratio of killed cockroaches. According to the results obtained, each $KT_{50}$ value (50% knock-down time) and mortality after 3 days are shown in the following Table 7.

0.05%, 0.15%, 0.6% of the present ester were formulated according to below-mentioned Example 1.

Into a (70 cm)³ Peet Grady chamber were liberated 50 Northern house mosquito adults (Female), and battery-driven small electric fan was rotated in the chamber. Thereafter, each of the mosquito coils of 0.8 g was ignited at one end, burned in the chamber and then removed. After ignition of the mosquito coil, the number of knocked down mosquitoes was counted with the lapse of time for 120 minutes to calculate the knock-down ratio of the mosquitoes. The results obtained are as shown in Table 8.

Table 8

| Test Compound | (Effects of mosquito coils on Northern house mosquitoes) | | | | | | | | | $KT_{50}$ (min) | Relative effect |
| --- | --- | --- | --- | --- | --- | --- | --- | --- | --- | --- | --- |
| | Knock-down (%) | | | | | | | | | | |
| | 1.25' | 2.5' | 5' | 10' | 20' | 40' | 60' | 90' | 120' | | |
| d-trans-chrysanthemic acid ester of dl-allethrolone (0.15 %) | 0 | 0 | 4 | 25 | 51 | 70 | 85 | 82 | 82 | 19.5 | 1.0 |
| Present ester (0.05 %) | 0 | 0 | 7 | 30 | 58 | 85 | 83 | 83 | 83 | 16.5 | 1.2 |
| Present ester (0.15 %) | 12 | 29 | 55 | 80 | 92 | 95 | 96 | 96 | 97 | 4.4 | 4.4 |
| Present ester (0.6 %) | 21 | 64 | 82 | 95 | 98 | 100 | 100 | 100 | 100 | 2.0 | 9.8 |

Figure 4:
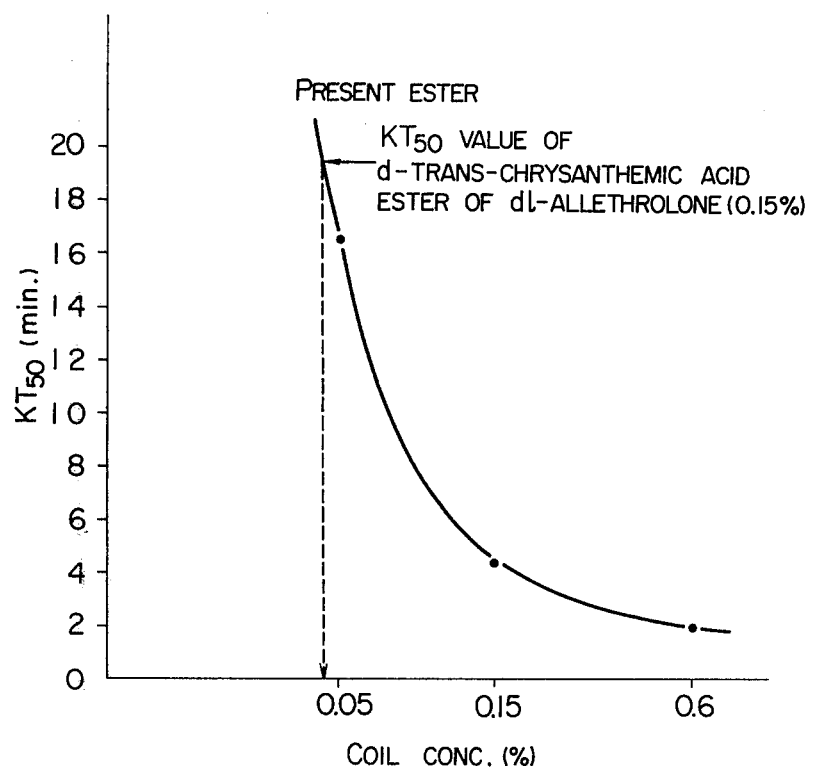
FIG. 4 shows the relation between a concentration and $KT_{50}$ in the knock-down effects of the mosquito coils on Northern house mosquito adults.

As is clear from Table 8, 0.15% mosquito coil containing the present ester has 4.4 times higher activity compared with 0.15% mosquito coil containing d-trans-chrysanthemic acid ester of dl-allethrolone and further, as is clear from FIG. 4, the effective concentration of mosquito coil containing present ester corresponding to the effective concentration of 0.15% mosquito coil containing d-trans-chrysanthemic acid ester of dl-allethrolone is 0.045% by weight, and therefore is one third.

Effect of the mosquito coil containing the present ester is 3.3 – 4.4 times higher than that of the dl-allethrolone ester, and therefore, in comparison with 2 times higher activity according to oil sprays stated in Table 7

| Test Compound | (Fogging effects on German cockroaches) | | | | | $KT_{50}$ (min) | Relative effect | Mortality (%) |
| --- | --- | --- | --- | --- | --- | --- | --- | --- |
| | Knock-down (%) | | | | | | | |
| | 1.25' | 2.5' | 5' | 10' | 20' | | | |
| d-trans-chrysanthemic acid ester of dl-allethrolone | 0 | 15 | 35 | 55 | 85 | 7 | 1.0 | 30 |
| Present ester | 40 | 85 | 95 | 100 | 100 | 1.6 | 4.4 | 95 |

Experimental Examples 1 and 2 above the present ester showed the surprisingly effective insecticidal activity when the present ester was used as a heating fumigant. The present ester can be formulated according to the conventional procedure into a markedly effective electric mosquito killer mat by incorporating in an amount of 0.05 to 90% by weight into pulp, fiber or the like substratum and then the resulting fumigant is placed on a hot plate heated by means of electric power or the like to a temperature of 120° to 400° C, whereby the active ingredient diffuses with the lapse of time to display a fumigant effect for a long period of time. Alternatively, the present ester is formulated into a markedly effective mosquito coil by incorporating in an amount of 0.05 to 5% by weight of the present ester as an active ingredient into a mosquito coil carrier. Still alternatively, the present ester is formulated into an oil solution of 0.05 to 90% by weight concentration, and the oil solution is ascended by capillary action through a lamp-wick or the like and then heated; and the present ester is formulated by conventional method into an oil preparation containing 0.05 to 90% by weight of the active ingredient or an emulsion containing 1 to 50% by weight of the active ingredient, and a solution obtained by diluting the oil preparation or emulsion with water is sprayed to dash through a heated cylinder or sprayed to a heated plate whereby the solution become foggy in the air owing to heat, whereby a fumigant effect can be displayed as well.

The present ester, which is an active ingredient of the present compositions, may not only be used singly but may be incorporated with, as stabilizers, suitable amounts of phenol or bisphenol derivatives such as BHT or the like, or arylamines such as phenyl-$\alpha$-naphthylamine, phenyl-$\beta$-naphthylamine or condensation product of phenetidine with acetone, whereby compositions which have been more stabilized in insecticidal effects can be obtained. Further, the compositions may be increased in insecticidal activity by incorporation of synergists for pyrethroid type insecticides such as $\alpha$-[2-(2-butoxyethoxy)ethoxy]-4, 5-methylenedioxy-2-propyltoluene (hereinafter referred to as "piperonyl butoxide"), N-(2-ethylhexyl)-bicyclo(2,2,1) hepta-5-ene-anhydrophthalic acid-2,3-dicarboximide (hereinafter referred to as "MGK-264") and the like.

Procedures for the preparation of the present compositions and effects thereof are illustrated below with reference to examples and test examples, but it is needless to say that the scope of the present invention is not limited to the examples.

EXAMPLE 1

A solution of 0.3 g of the present ester in 5 ml of methanol is thoroughly mixed with a mixture comprising 60 g of pyrethrum marc, 30 g of Tabu powder and 9.7 g of wood powder. The resulting mixture is kneaded with about 100 ml of water, and then shaped and dried to prepare 100 g of a mosquito coil.

If necessary, the product may be colored by addition of 0.5% of Malachite Green or the like dye, or may be incorporated with phenol or para-hydroxybenzoate.

EXAMPLE 2

A solution of 0.04 g of the present ester and 0.06 g of piperonylbutoxide in chloroform is uniformly absorbed on the surface of an asbestos piece of 2.5 cm × 1.5 cm in area and 0.3 cm in thickness (4 g). Onto the thus treated asbestos piece is adhered another asbestos piece same in size to obtain an insecticidal fumigant composition for use on an electrically heated plate.

As the fibrous support, there may be used, in addition to asbestos, a pulp plate or the like material equal in effect to asbestos.

EXAMPLE 3

A solution of 0.2 g of the present ester and 0.6 g of MGK-264 in 5 ml methanol is added to a mixture comprising 60 g of pyrethrum marc, 30 g of Tabu powder and 9.2 g of wood powder, and the resulting mixture is treated in the same manner as in Example 1 to obtain a mosquito coil.

Insecticidal effects of the present compositions obtained in the above manner are shown below with reference to test examples.

TEST EXAMPLE 6

In a (70 cm)$^3$ glass chamber were liberated about 50 adults of Northern house mosquitoes, and 0.2 g of each of the mosquito coils obtained according to Examples 1 and 3 was ignited on both ends and placed at the center of the bottom of the chamber. Subsequently, the smoke inside the chamber was stirred by means of a small electric fan of 13 cm in blade diameter, whereby each of the mosquito coils could knock down within 15 minutes more than 90% of the mosquito adults.

TEST EXAMPLE 7

Into a (70 cm)$^3$ glass chamber were liberated about 50 adults of houseflies. The insecticidal fumigant composition obtained according to Example 2 was placed on an electric heating means and placed at the center of the bottom of the chamber, and an electric current was applied to said electric heating means. Subsequently, the interior of the chamber was stirred by means of a small electric fan of 13 cm in blade diameter, whereby more than 90% of the housefly adults could be knocked down within 20 minutes.

TEST EXAMPLE 8

Into a Peet Grady chamber according to the U.S. CSMA standard, was liberated about 500 adults of houseflies. An emulsion of the present ester obtained by diluting the ordinarily prepared 20% emulsion with 20 times the volume of water was fogged by means of an Insect Fogger produced by Burgess Vibrocrafters, INC. into the chamber above mentioned, and more than 90% of the adults could be knocked down within 30 minutes.

What is claimed is:

1. An insecticidal material consisting essentially of an insecticidally effective amount of d-2-allyl-3-methyl-cyclopent-2-ene-1-one-4-yl d-trans-chrysanthemate absorbed on a fibrous support suitable for use on an electrically heated plate.

2. A method for killing insects selected from the group consisting of mosquitoes, houseflies and cockroaches, which comprises subjecting said insects to an insecticidally effective amount of d-2-allyl-3-methyl-cyclopent-2-ene-1-one-4-yl d-trans-chrysanthemate in the form of a vapor produced by heating the material of claim 1 on an electrically heated plate.

* * * * *